United States Patent
Kuma et al.

(10) Patent No.: US 10,774,038 B2
(45) Date of Patent: Sep. 15, 2020

(54) PROCESS FOR PRODUCING CYANONORBORNENE

(71) Applicant: MITSUI CHEMICALS, INC., Minato-ku, Tokyo (JP)

(72) Inventors: Shigetoshi Kuma, Kurume (JP); Tomoya Sanda, Omuta (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 0 days.

(21) Appl. No.: 16/634,929

(22) PCT Filed: Jul. 23, 2018

(86) PCT No.: PCT/JP2018/027459
§ 371 (c)(1),
(2) Date: Jan. 29, 2020

(87) PCT Pub. No.: WO2019/026664
PCT Pub. Date: Feb. 7, 2019

(65) Prior Publication Data
US 2020/0239408 A1    Jul. 30, 2020

(30) Foreign Application Priority Data
Jul. 31, 2017   (JP) .................. 2017-148428

(51) Int. Cl.
C07C 253/30    (2006.01)
C07C 255/47    (2006.01)

(52) U.S. Cl.
CPC .......... *C07C 253/30* (2013.01); *C07C 255/47* (2013.01); *C07C 2602/46* (2017.05)

(58) Field of Classification Search
CPC .. C07C 253/30; C07C 2602/46; C07C 255/47
USPC ......................................................... 558/351
See application file for complete search history.

(56) References Cited

U.S. PATENT DOCUMENTS

| | | | |
|---|---|---|---|
| 6,441,259 | B1 | 8/2002 | Aida et al. |
| 9,487,475 | B2 | 11/2016 | Tokunaga et al. |
| 2015/0299109 | A1 | 10/2015 | Tokunaga et al. |

FOREIGN PATENT DOCUMENTS

| | | |
|---|---|---|
| JP | 2002069008 A | 3/2002 |
| JP | 2002348271 A | 12/2002 |
| JP | 2002348272 A | 12/2002 |
| WO | 0134540 A1 | 5/2001 |
| WO | 2014073664 A1 | 5/2014 |

OTHER PUBLICATIONS

International Search Report (PCT/ISA/210) and translation and Written Opinion (PCT/ISA/237) dated Oct. 16, 2018, by the Japanese Patent Office as the International Searching Authority for International Application No. PCT/JP2018/027459.

*Primary Examiner* — Kristin A Vajda
(74) *Attorney, Agent, or Firm* — Buchanan, Ingersoll & Rooney PC

(57) ABSTRACT

A process for producing cyanonorbornene of the present invention includes Step 1 of preparing a mixture solution including 0.5% by weight to 28% by weight of methyl bicyclononadiene, with respect to a total amount of 100% by weight of dicyclopentadiene, acrylonitrile, and the methyl bicyclononadiene, in a container, and Step 2 of reacting the bicyclopentadiene with the acrylonitrile in the presence of the methyl bicyclononadiene, in the mixture solution.

6 Claims, 1 Drawing Sheet

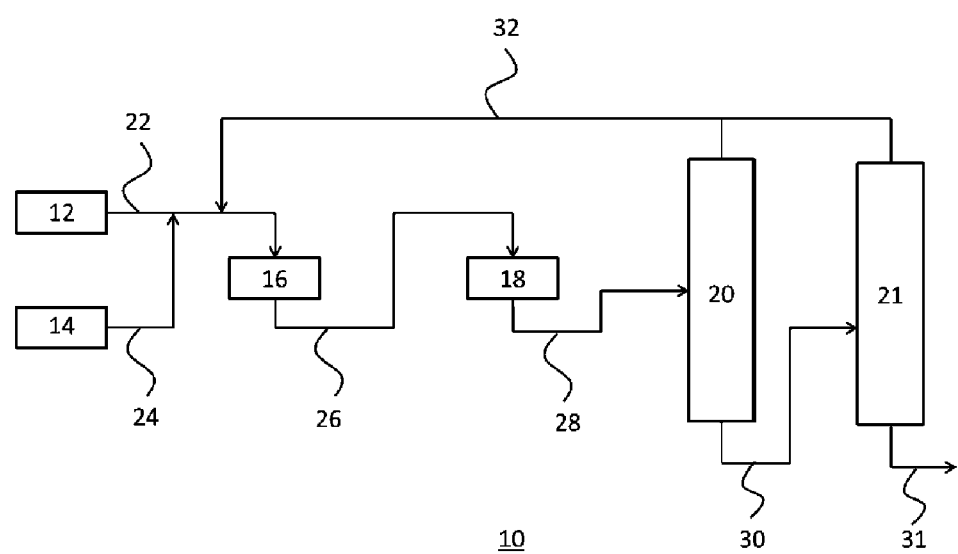

PROCESS FOR PRODUCING CYANONORBORNENE

TECHNICAL FIELD

The present invention relates to a process for producing cyanonorbornene by using dicyclopentadiene and acrylonitrile.

BACKGROUND ART

A process for producing cyanonorbornene by using dicyclopentadiene and acrylonitrile is described in Patent Documents 1 and 2, for example.

Patent Documents 1 and 2 disclose a method of recovering acrylonitrile and cyclopentadiene or dicyclopentadiene which are non-reactive raw materials included in a reaction product when producing cyanonorbornene by consecutively reacting cyclopentadiene or dicyclopentadiene and acrylonitrile and reusing thereof as a raw material. Examples and the like of Patent Documents 1 and 2 disclose that the reaction system includes methyl bicyclononadiene.

Patent Document 3 discloses that tetrahydroindene has low reactivity in the Diels-Alder reaction and a high decomposition temperature, and thus is mixed in a raw material compound for circulative reuse and accumulated in the system. In addition, since tetrahydroindene has an impact on reaction, there is disclosed a method of reducing the compound.

Patent Document 4 discloses a process for producing an amine compound by using cyanonorbornene or a process for producing an isocyanate compound by using the amine compound.

RELATED DOCUMENTS

Patent Documents

[Patent Document 1] JP2002-348271
[Patent Document 2] JP2002-348272
[Patent Document 3] JP2002-069008
[Patent Document 4] WO2014/073664

SUMMARY OF THE INVENTION

Technical Problem

The techniques described in the documents have room for improvement in the following points.

In the techniques of Patent Documents 1 and 2, when a reaction step between dicyclopentadiene and acrylonitrile, a step of recovering a non-reactive raw material, and a step of reusing thereof as a raw material are consecutively repeatedly performed, there was a case where a temperature of a reaction solution was decreased, and an excessive increase in the temperature of the reaction solution was required to continue reaction. For this reason, there was a case where a production step becomes inconvenient, and the production cost is increased. In addition, there was room for improvement in a yield of cyanonorbornene.

The present inventors paid attention to methyl bicyclononadiene having a low calorific value than that of dicyclopentadiene in the Diels-Alder reaction. In a case of reusing a raw material compound, the compound was mixed with the raw material compound and accumulated in the system, and it was not possible to ensure a calorific value required for the Diels-Alder reaction. Therefore, it is considered that an excessive increase in the temperature is required to maintain a reaction rate or yield, and it is preferable to remove the compound from the reaction system as much as possible. However, in order to remove most methyl bicyclononadiene from the reaction system, a purification step of the raw material compound becomes complicated, and a lot of purification time is required. For this reason, if a permissible amount of methyl bicyclononadiene contained in the reaction system can be found, there are extreme advantages in the production of cyanonorbornene. On the other hand, surprisingly, it was found that, in order to proceed the Diels-Alder reaction at a high yield, there is a need that a certain amount or more of methyl bicyclononadiene is contained.

Solution to Problem

As a result of intensive examination, the present inventors found that if the amount of methyl bicyclononadiene which is impurities present in the reaction system is within a predetermined range, these points are resolved, and completed the invention.

That is, the present invention can be seen as follows.

[1] A process for producing cyanonorbornene, including: Step 1 of preparing a mixture solution including 0.5% by weight to 28% by weight of the methyl bicyclononadiene with respect to 100% by weight of a total amount of dicyclopentadiene, acrylonitrile, and the methyl bicyclononadiene, in a container; and Step 2 of reacting the dicyclopentadiene and the acrylonitrile in the presence of the methyl bicyclononadiene in the mixture solution.

[2] The process for producing cyanonorbornene according to [1], further including: Step 3 of obtaining cyanonorbornene from a reaction product obtained in Step 2, after Step 2, and recovering the methyl bicyclononadiene and a non-reactive raw material, and Step 4 of providing the recovered methyl bicyclononadiene and the non-reactive raw material to the container in Step 1 and reusing thereof, in which Steps 1 to 4 are consecutively repeatedly performed.

[3] The process for producing cyanonorbornene according to [1] or [2], in which the reaction product obtained in Step 2 includes 0.5% by weight to 28% by weight of the methyl bicyclononadiene with respect to a total amount of 100% by weight of the cyanonorbornene, the methyl bicyclononadiene, and the non-reactive raw material.

[4] The process for producing cyanonorbornene according to any one of [1] to [3], in which a reaction temperature in Step 2 is 160° C. to 220° C.

[5] A process for producing an amine compound, including: a step of preparing cyanonorbornene by the production method according to anyone of [1] to [4], a step of performing hydroformylation reaction on the cyanonorbornene with carbon monoxide and hydrogen, and a step of performing imination by reacting an aldehyde compound obtained in the hydroformylation step with ammonia and reacting thereof with hydrogen in the presence of a catalyst.

[6] A process for producing an isocyanate compound, including: a step of preparing an amine compound by the production method according to [5], and a step of reacting the amine compound with a carbonylating agent.

Advantageous Effects of Invention

According to the process for producing cyanonorbornene of the present invention, since a decrease in a temperature of a reaction solution is suppressed, an excessive increase in the temperature of the reaction solution is not required to continue reaction, production steps become simple, and the production cost can be suppressed. In addition, a yield of cyanonorbornene is also excellent. That is, the present invention is excellent in balance between simplification of the production step of cyanonorbornene or suppression of the production cost and improvement in the yield of cyanonorbornene.

BRIEF DESCRIPTION OF THE DRAWINGS

The above-described object, objects other than the object, features, and advantages become further apparent by appropriate embodiments and accompanying drawings to be described later.

FIG. 1 is a production flow diagram of cyanonorbornene of a second embodiment.

DESCRIPTION OF EMBODIMENTS

[Process for Producing Cyanonorbornene]

Hereinafter, a process for producing cyanonorbornene of the present invention will be described with first and second embodiments.

First Embodiment

A process for producing cyanonorbornene of the present embodiment includes the following steps.

Step 1: 0.5% by weight to 28% by weight of a mixture solution of methyl bicyclononadiene with respect to 100% by weight of a total amount of dicyclopentadiene, acrylonitrile, and the methyl bicyclononadiene is prepared in a container.

Step 2: In the mixture solution, the dicyclopentadiene and the acrylonitrile are reacted in the presence of the methyl bicyclononadiene to synthesize cyanonorbornene.

(Step 1)

Dicyclopentadiene used as a raw material is obtained by dimerizing cyclopentadiene under a condition of a normal temperature and a normal pressure. Since the dicyclopentadiene is decomposed under a reaction condition to generate cyclopentadiene, dicyclopentadiene is generally used in reaction. In the present embodiment, it is preferable to use dicyclopentadiene, and it is described by an example in which dicyclopentadiene was used. In the present embodiment, dicyclopentadiene used as a raw material is recovered from a thermal decomposition oil such as naphtha, and engineeringly obtained by a large amount. Dicyclopentadiene includes methyl bicyclononadiene as impurities.

In a mixture solution, an upper limit value of the content of methyl bicyclononadiene is 0.5% by weight to 28% by weight, preferably 0.5% by weight to 25% by weight, more preferably 0.5% by weight to 21% by weight, further more preferably 0.5% by weight to 10% by weight, and most preferably 0.5% by weight to 5% by weight, with respect to 100% by weight of the total amount of dicyclopentadiene, acrylonitrile, and methyl bicyclononadiene.

In the range, in the reaction of Step 2, since a decrease in a temperature of a reaction solution is suppressed, an excessive increase in the temperature of the reaction solution is not required to continue reaction, production steps become simple, and the production cost can be suppressed. In addition, a yield of cyanonorbornene is excellent.

Methyl bicyclononadiene contained in the mixture solution is Compound (1) derived from impurities contained in dicyclopentadiene. In a case where a non-reactive raw material including methyl bicyclononadiene (2), which is recovered after Step 2, is used in Step 1, an amount of methyl bicyclononadiene is a total amount of Compound (1) and Compound (2).

As acrylonitrile used as a raw material, for example, acrylonitrile engineeringly manufactured by a large amount such as ammoxidation of propylene can be used.

In the present embodiment, a mixture solution including dicyclopentadiene, acrylonitrile, and methyl bicyclononadiene is prepared in a container. As the mixture method, a known conventional method can be employed.

(Step 2)

In the mixture solution including methyl bicyclononadiene in the range, obtained in Step 1, dicyclopentadiene and acrylonitrile are reacted in the presence of methyl bicyclononadiene to synthesize cyanonorbornene represented by the following chemical formula (1). The compound represented by the chemical formula (1) may be any of an end body or exo body or may be a mixture including thereof at an optional ratio.

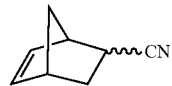

(1)

In the present step, a reaction temperature can be within a range of 160° C. to 220° C., but is preferably within a range of 180° C. to 210° C. Since a thermal decomposition temperature of dicyclopentadiene to cyclopentadiene is 160° C., reaction is slow at less than 170° C. and is not practical. A reaction pressure can be within a range of 0.6 MPa·G or more and 3 MPa·G or less, preferably within a range of 0.6 MPa·G or more and 1.5 MPa·G or less, and more preferably within a range of 0.6 MPa·G or more and 0.9 MPa·G or less.

A retention time varies depending on the reaction temperature and thus cannot be generally said, but considering the yield and the productivity, the retention time is generally within a range of 0.1 hour to 10 hours. In addition, depending on the necessity, it does not matter whether to shorten the retention time, or lengthen the retention time.

Reaction between acrylonitrile and dicyclopentadiene is in theory, reaction of 2 mol acrylonitrile with respect to 1 mol of dicyclopentadiene, but the mixture raw material is generally preferably within a range of 2 mol to 3 mol of acrylonitrile with respect to 1 mol of dicyclopentadiene.

It is known that isopropenyl norbornene which is one of impurities in dicyclopentadiene is isomerized in thermal reaction to generate methyl bicyclononadiene (Bulletin of The Chemical Society of Japan, Vol. 49(7), 2017-2018 (1976)). Some of isopropenyl norbornene in dicyclopentadiene which is a raw material is isomerized to generate methyl bicyclononadiene.

For this reason, a reaction product obtained in Step 2 can include the methyl bicyclononadiene by an amount of 0.5% by weight to 28% by weight, preferably 0.5% by weight to 25% by weight, more preferably 0.5% by weight to 21% by weight, further more preferably 0.5% by weight to 10% by weight, and most preferably 0.5% by weight to 5% by weight, with respect to a total amount of 100% by weight of cyanonorbornene, methyl bicyclononadiene, and a non-reactive raw material. Within the range, even if methyl bicyclononadiene is accumulated in the reaction process, a decrease in a temperature of the reaction solution is more suppressed in reaction of Step 2 and is more excellent in a yield of cyanonorbornene.

After Step 2, when decomposing and recovering cyanonorbornene which is a target substance, it is possible to recover methyl bicyclononadiene and a non-reactive raw material (dicyclopentadiene, acrylonitrile). The recovered methyl bicyclononadiene and the non-reactive raw material can be used as raw materials of Step 1.

Second Embodiment

Hereinafter, a second embodiment of the present invention will be described using drawings. In all drawings, like components have like reference numerals, and appropriate description will not be repeated.

A process for producing cyanonorbornene of the present embodiment includes the following steps, and Steps 1 to 4 are consecutively repeatedly performed.

Step 1: A mixture solution including 0.5% by weight to 28% by weight of methyl bicyclononadiene with respect to a total amount of 100% by weight of dicyclopentadiene, acrylonitrile, and methyl bicyclononadiene is prepared in a container (mixer 16).

Step 2: In the mixture solution provided in a reaction vessel 18, the dicyclopentadiene and the acrylonitrile are reacted in the presence of the methyl bicyclononadiene.

Step 3: Cyanonorbornene is obtained from a reaction product obtained in Step 2, and the methyl bicyclononadiene and a non-reactive raw material are recovered.

Step 4: The recovered methyl bicyclononadiene and non-reactive raw material are provided in the container in Step 1 and reused.

The process for producing cyanonorbornene of the present embodiment will be described based on a production flow diagram 10 of FIG. 1. The reaction conditions in Steps 1 and 2 and the like are the same as those of the first embodiment, and appropriate description will not be repeated. The present embodiment will be described by an example in which dicyclopentadiene was used as a raw material.

(Step 1)

Acrylonitrile which is a raw material is consecutively provided to the mixer 16 from a tank 12 through a line 22. Dicyclopentadiene joins in the line 22 from a tank 14 through a line 24, and a mixture solution including the recovered methyl dicyclononadiene and a non-reactive raw material joins through a line 32 in Step 4 to be described later. With this, the mixture solution of dicyclopentadiene, acrylonitrile, and methyl bicyclononadiene is prepared in the mixer 16.

In the mixture solution, methyl bicyclononadiene is included by an amount of 0.5% by weight to 28% by weight, preferably 0.5% by weight to 25% by weight, more preferably 0.5% by weight to 21% by weight, further more preferably 0.5% by weight to 10% by weight, and most preferably 0.5% by weight to 5% by weight with respect to a total amount of 100% by weight of dicyclopentadiene, acrylonitrile, and methyl bicyclononadiene.

Within the range, since a decrease in a temperature of the reaction solution is suppressed in reaction of Step 2, an increase in the temperature of the reaction solution is not required to continue reaction, production steps become simple, and the production cost can be suppressed. In addition, it is excellent in a yield of cyanonorbornene.

The mixture solution obtained in the mixer 16 is consecutively provided to the reaction vessel 18 through a line 26.

For the purpose of suppressing a by-product of a polymer at the reaction vessel 18, it is preferable to add a compound that suppresses generation of the polymer in the mixture solution of the line 26. As a compound that suppresses generation of the polymer, a wide range of compounds, such as those used in the general Diels-Alder reaction known in the related art, can be used. Among these, in particular, it is extremely preferable to use an N-nitrosoamine compound or p-phenylene diamine compound. The compound may be one kind, or two or more kinds. A use amount of the compound that suppresses generation of the polymer is generally within a range of 0.003% by weight to 1% by weight, with respect to a total amount of a mixture raw material of the line 26.

(Step 2)

In the mixture solution provided in the reaction vessel 18, acrylonitrile and dicyclopentadiene are reacted in the presence of methyl bicyclononadiene to synthesize cyanonorbornene represented by the chemical formula (1). Reaction can be performed under the same conditions as those of Step 2 of the first embodiment.

As a reactor 4, a complete mix type stirring tank reactor, a piston flow type tubular reactor, or the like can be used, but it is preferable to use a stirring tank reactor in order to avoid clogging troubles or the like caused by adhesion of an insoluble polymer in a reactor or a pipe, or the like and to perform consecutive reaction for a long time.

The reaction product obtained in Step 2 can include the methyl bicyclononadiene by an amount of 0.5% by weight to 28% by weight, preferably 0.5% by weight to 25% by weight, more preferably 0.5% by weight to 21% by weight, further more preferably 0.5% by weight to 10% by weight, and most preferably 0.5% by weight to 5% by weight, with respect to a total amount of 100% by weight of cyanonorbornene, methyl bicyclononadiene, and a non-reactive raw material. Within the range, even if methyl bicyclononadiene is accumulated in the reaction process, a decrease in a temperature of the reaction solution is more suppressed in reaction of Step 2 and is more excellent in a yield of cyanonorbornene.

(Step 3)

The reaction product that is consecutively extracted through the line 28 from the reaction vessel 18 is provided to a flash device 20, and from a tower top portion of the flash device 20, the mixture solution including acrylonitrile and dicyclopentadiene which are non-reactive raw materials, and methyl bicyclononadiene is separated and recovered through a line 32. Through a line 30 from a tower bottom portion of the flash device 20, a high-concentration cyanonorbornene solution including non-reactive raw materials, methyl bicyclononadiene which is by-produced from the reaction, a high-boiled product, and the like by a small amount is provided to a raw material recovering tower 21 through the line 30.

Operating conditions in the flash device 20 are preferably a temperature of 100° C. to 180° C. and a normal pressure.

From the tower top portion of the raw material recovering tower 21, a mixture solution including acrylonitrile and dicyclopentadiene which are non-reactive raw materials, methyl bicyclononadiene, and water is obtained, and is separated and recovered through the line 32 in a state in which water has been separated from the solution. Through a line 31 from the tower bottom portion of the raw material recovering tower 21, a high-concentration cyanonorbornene including a high-boiled product and the like by a small amount is obtained.

Operating conditions in the raw material recovering tower 21 are preferably a tower bottom portion temperature of 100° C. to 150° C., a tower bottom portion pressure of 12 kPa to 25 kPa, a tower top portion temperature of 50° C. to 120° C., and a tower top portion pressure of 11 kPa to 23 kPa.

The cyanonorbornene solution separated from the line 31 has high concentration as it is, but a purity may be enhanced by further performing optional purification such as rectification depending on the use of cyanonorbornene.

(Step 4)

Through the line 32, the recovered mixture solution including acrylonitrile, dicyclopentadiene, and methyl bicyclononadiene is provided to a mixing vessel 16 through the line 22 and reused in reaction.

[Process for Producing Amine Compound]

A process for producing an amine compound of the present invention will be described with first and second embodiments.

First Embodiment

A process for producing an amine compound of the present embodiment includes the following steps.

Step a1: Cyanonorbornene obtained by the above-described production method is hydroformylation-reacted with carbon monoxide and hydrogen to synthesize an aldehyde compound.

Step a2: The aldehyde compound obtained in Step a is reacted with ammonia to iminize thereof, and is reacted with hydrogen in the presence of a catalyst to synthesize an amine compound.

(Step a1)

(Process for Producing Aldehyde Compound)

In the present step, cyanonorbornene is reacted with hydrogen and carbon monoxide in the presence of a metal compound and a phosphorus compound including Groups 8 to 10 metal.

As a metal compound including Groups 8 to 10 metal, a rhodium compound, a cobalt compound, a ruthenium compound, an iron compound, and the like can be exemplified. As the phosphorus compound, a trivalent phosphorus compound can be exemplified.

As the rhodium compound, for example, $Rh(acac)(CO)_2$, $Rh(acac)_3$, $RhCl(CO)(PPh_3)_2$, $RhCl(PPh_3)_3$, $RhBr(CO)(PPh_3)_2$, $Rh_2(CO)_8$, $Rh_4(CO)_{12}$, $Rh_6(CO)_{16}$, and the like are exemplified. As the cobalt compound, for example, $HCo(CO)_3$, $HCo(CO)_4$, $Co_2(CO)_8$, $HCo_3(CO)_9$, and the like are exemplified. As the ruthenium compound, for example, $Ru(CO)_3(PPh3)_2$, $RuCl2(PPh3)3$, $RuCl_3(PPh_3)_3$, $Ru_3(CO)_{12}$, and the like are exemplified. In addition, as the iron compound, for example, $Fe(CO)_5$, $Fe(CO)_4PPh_3$, $Fe(CO)_4(PPh_3)_2$, and the like are exemplified. "acac" means acetyl acetonate.

The rhodium compound used in reaction of the present embodiment is not particularly limited as long as the compound is a compound including monovalent rhodium metal, but examples thereof can include a rhodium carbonyl catalyst such as dicarbonyl acetylacetonate rhodium ($Rh(acac)(CO)_2$), dodecacarbonyl tetrarhodium ($Rh_4(CO)_{12}$), hexadecacarbonyl hexarhodium ($Rh_6(CO)_{16}$), and octacarbonyl dirhodium ($Rh_2(CO)_8$); rhodium chloride, and the like.

The phosphorus compound used in reaction of the present embodiment is not particularly limited as long as the compound is a trivalent phosphorus compound, but a compound presented by the following formula is preferably used.

$(R^1)_3P$ $(R^2O)_3P$

In the formula, $R^1$, $R^2$ may be the same or different, and indicate an alkyl group having 1 to 16 carbons or an aryl group having 6 to 16 carbons that may have a substituent, respectively.

As the phosphorus compound, specifically, examples thereof include a trivalent phosphorus compound such as triphenyl phosphite, triphenyl phosphine, trimethyl phosphine, triethyl phosphine, triprophyl phosphine, tri(methylbenzene)phosphine, tri(ethylbenzene)phosphine, 1,2-bis(diphenyl phosphino)ethylene, 1,3-bis(diphenyl phosphino) propane, 2,2-bis(diphenyl phosphino)-1,1-binaphthyl, trimethoxy phosphite, triethoxy phosphite, tripropoxy phosphite, triisopropoxy phosphite, trimethylphenyl phosphite, and tris(2,4-di-tert-butylphenyl)phosphite.

In hydroformylation reaction using the raw materials and the like, an amount of Groups 8 to 10 metal to be used is 0.01 ppm mol to 10 ppm mol, preferably 1 ppm mol to 10 ppm mol, and more preferably 1 ppm mol to 5 ppm mol, with respect to 1 mol of a compound (a1). Within the numerical value range, it is possible to ensure proceeding of smooth reaction without excessively using an expensive catalyst.

In addition, an amount of the phosphorus compound to be used is 100 times mol or more, and more preferably 100 times mol to 10,000 times mol, with respect to Groups 8 to 10 metal.

The numerical value range can be optionally combined.

Synthesis of the aldehyde compound can be specifically performed as follows.

First, a rhodium compound, a phosphorus compound, and cyanonorbornene of raw materials are inserted into the container. Here, while providing hydrogen and carbon monoxide gas, synthesis can be performed at a temperature of 30° C. to 120° C., a pressure of 0.1 MPa to 1.0 MPa, and a reaction time of 1 to 8 hours. Hydroformylation reaction can be performed by appropriately selecting a homogeneous reaction system of only an oil phase or a double layer reaction system formed of a water layer and an oil layer.

With this, hydroformylation is performed on cyanonorbornene to synthesize the aldehyde compound.

The hydroformylation reaction can be performed in a solvent-free agent, a substituted or non-substituted aromatic compound, a substituted or non-substituted aliphatic hydrocarbon compound, and alcohol can be used, and the hydroformylation reaction can be also performed in a solvent such as toluene, benzene, hexane, octane, acetonitrile, benzonitrile, orthodichlorobenzene, ethanol, pentanol, and octanol. Since the hydroformylation reaction in the present embodiment is excellent in reactivity in high concentration, it is possible to perform the hydroformylation reaction in a solvent-free agent. With this, since a step of distilling a solvent and the like are not required, the step becomes simple, volume efficiency is also improved, and production efficiency is also excellent.

By the production method of the present embodiment, an aldehyde compound represented by the following general formula (2) is synthesized from the compound of the general formula (1).

(2)

The aldehyde compound represented by the general formula (2) can be obtained as any one of "a compound in which bicyclo[2.2.1]heptane at a second position is substituted with a cyano group, and bicyclo[2.2.1]heptane at a fifth position is substituted with an aldehyde group (hereinafter, 2, 5 body), or "a compound in which bicyclo[2.2.1]heptane at a second position is substituted with a cyano group, and bicyclo[2.2.1]heptane at a sixth position is substituted with an aldehyde group (hereinafter, 2, 6 body)" or as a mixture including thereof at an optional ratio. In addition, each of the 2, 5 body and the 2, 6 body can be obtained as any one of an end-end body, an end-exo body, and an exo-exo body by steric arrangement of a substituent or can be also obtained as a mixture including at least two kinds thereof at an optional ratio.

After finishing the hydroformylation reaction, it is possible to perform a predetermined purification step and to obtain a targeted aldehyde compound.

(Step a2)

(Process for Producing Amine Compound)

A process for producing an amine compound of the present embodiment includes the following steps.

Step (a): Using a compound (1) including acrylonitrile within a predetermined range, the compound (1) is reacted with hydrogen and carbon monoxide in the presence of a metal compound including 8 to 10 group metals and a phosphorus compound.

Step (b): An aldehyde compound obtained in Step (a) is reacted with ammonia, and reacted with hydrogen in the presence of a catalyst.

The process for producing an amine compound of the present embodiment includes the process for producing the aldehyde compound as Step (a). For this reason, in Step (a), since it is possible to produce the aldehyde compound by an industrially advantageous method in the method of the present invention, the method is also excellent in improvement of productivity and yield of an amine compound which is a target compound.

Since Step (a) is the same as that of the step in the "process for producing aldehyde compound", description will not be repeated.

In Step (b), imination is performed by reacting the aldehyde compound represented by the general formula (2) obtained in Step (a) with ammonia, and an amine compound is synthesized by adding hydrogen in the presence of a catalyst.

As a catalyst, it is possible to use a metal catalyst such as nickel, platinum, palladium, ruthenium and the like. In a case where the aldehyde compound includes a cyano group as a substituent, a —CH$_2$—NH$_2$ group is generated by hydrogen reduction.

With this, in Step (b), since an aldehyde group included in the aldehyde compound becomes an amino group by imination, and the cyano group also becomes an amino group by hydrogen reduction, an amine compound represented by the following chemical formula (3), which has two amino groups, is synthesized.

(3)

The amine compound represented by the chemical formula (3) can be obtained as any one of "a compound in which bicyclo[2.2.1]heptane at a second position and a fifth position is substituted with an amino methyl group (hereinafter, 2, 5 body), or "a compound in which bicyclo[2.2.1]heptane at a second position and a sixth position is substituted with an amino methyl group (hereinafter, 2, 6 body)" or as a mixture including thereof at an optional ratio. In addition, each of the 2, 5 body and the 2, 6 body can be obtained as any one of an end-end body, an end-exo body, and an exo-exo body, by steric configuration of a substituent, or can be also obtained as a mixture including at least two kinds thereof at an optional ratio.

The imination and hydrogen addition reaction can be specifically performed as follows. First, an aldehyde compound, a solvent, and a catalyst are put in a reaction vessel, and ammonia gas is blown therein. Then, hydrogen is pressed in up to a pressure of about 1 MPa, a temperature is increased to about 100° C., and reaction is performed for 1 to 10 hours, under the temperature and the pressure, while providing hydrogen. As a catalyst, for example, alcohol having 1 to 8 carbon atoms, water, and the like are appropriately used.

In addition, after finishing the reaction, it is possible to perform general catalyst filtration, desolventizing, purification step, and the like, and to obtain a targeted amine compound.

Second Embodiment

A process for producing an amine compound of the present embodiment includes the following steps.

Step b1: Hydrogen cyanide is reacted with cyanonorbornene obtained by the above-described production method.

Step b2: Hydrogen is added to dicyanonorbornenes obtained in the step b1 in the presence of a catalyst to synthesize an amine compound.

(Step b1)

(Process for Producing Dicyanonorbornenes)

In the present step, it is possible to react hydrogen cyanide with cyanonorbornene in the presence of a zero-valent nickel complex catalyst to synthesize dicyanonorbornenes.

A use amount of hydrogen cyanide can be an optional molar amount with respect to 1 mol of cyanonorbornene, but is generally 1 mol. In addition, a reaction temperature of reaction of hydrogen cyanide and cyanonorbornene is preferably −20° C. to 200° C., more preferably 0° C. to 130° C., and further more preferably 20° C. to 100° C. The reaction pressure may be normal pressure or increased pressure, but since there is no remarkable reaction promoting effect due to an increase in pressure, the step is generally performed under the normal pressure.

In the present embodiment, as a reaction mode of reaction of hydrogen cyanide and cyanonorbornene, normal batch type is employed, but consecutive type is also employed so as to consecutively provide cyanonorbornene, hydrogen cyanide, a zero-valent nickel complex catalyst synthesis solution, or, depending on the necessity, a solvent and the like. By the present step, it is possible to obtain dicyanonorbornenes represented by the following chemical formula (4).

(4)

(Step b2)
(Process for Producing Amine Compound)

In the present step, an aldehyde compound obtained in the step b1 is hydrogen-added in the presence of a catalyst to synthesize an amine compound.

As a catalyst, it is possible to use a metal catalyst such as nickel, platinum, palladium, ruthenium, and the like.

The hydrogen addition reaction can be specifically performed as follows.

First, an aldehyde compound, a solvent, and a catalyst are put in a reaction vessel. Then, hydrogen is pressed in up to a pressure of about 1 MPa, a temperature is raised to about 100° C., and reaction is performed for 1 to 10 hours, under the temperature and the pressure, while providing hydrogen. As the catalyst, for example, alcohol having 1 to 8 carbon atoms, water, and the like are appropriately used.

In addition, after finishing the reaction, it is possible to perform general catalyst filtration, desolventizing, purification step, and the like, and to obtain a targeted amine compound represented by the chemical formula (3).

[Process for Producing Isocyanate Compound]

A process for producing an isocyanate compound of the present embodiment includes the following steps.

Step (a): Using a compound (1) including acrylonitrile within a predetermined range, the compound (1) is reacted with hydrogen and carbon monoxide in the presence of a metal compound including 8 to 10 group metals and a phosphorus compound.

Step (b): The aldehyde compound obtained in Step (a) is reacted with ammonia, and is reacted with hydrogen in the presence of a catalyst.

Step (c): An amine compound obtained in Step (b) is reacted with a carbonylating agent.

A process for producing an isocyanate compound of the present embodiment includes a process for producing the above-described aldehyde compound as Step (a). For this reason, in Step (a), since it is possible to produce the aldehyde compound by an industrially advantageous method in the method of the present invention, the method is also excellent in productivity and yield of an isocyanate compound which is a target compound.

Since Step (a) is the same as the step in the "process for producing an aldehyde compound", and Step (b) is the same as the step in the "process for producing an amine compound", description will not be repeated.

In Step (c), an amine compound represented by the chemical formula (3) obtained in Step (b) is reacted with a carbonylating agent under a predetermined condition to synthesize an isocyanate compound represented by the following chemical formula (5).

As the carbonylating agent, it is possible to use phosgene, a urea derivative, a carbonate derivative, carbon monoxide, and the like.

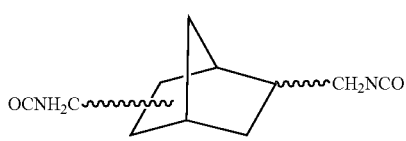

(5)

An isocyanate compound represented by the chemical formula (5) can be obtained as any one of "a compound in which bicyclo[2.2.1]heptane at a second position and a fifth position is substituted with an isocyanato methyl group (hereinafter, 2, 5 body), or "a compound in which bicyclo[2.2.1]heptane at a second position and a sixth position is substituted with an isocyanato methyl group (hereinafter, 2, 6 body)" or as a mixture including thereof at an optional ratio. In addition, each of the 2, 5 body and the 2, 6 body can be obtained as any one of an end-end body, an end-exo body, and an exo-exo body by steric arrangement of a substituent, or can be also obtained as a mixture including at least two kinds thereof at an optional ratio.

In a case where phosgene is used as a carbonylating agent, examples of Step (c) can specifically include a method of first putting an amine compound and a solvent in a reaction vessel and reacting thereof with phosgene after being chloridated with a hydrochloric acid, a method of obtaining a carbamoyl chloride compound by directly performing reaction with phosgene, and then performing thermal decomposition, and the like. In addition, after finishing the reaction, it is possible to perform a general purification step and the like, and to obtain a targeted isocyanate compound.

A reaction solvent in a case where phosgene is used as a carbonylating agent is not particularly limited, but it is preferable to use a high-boiling point organic aromatic compound or ester compound in which solubility of the hydrochloric acid is large at the time of salt production reaction, solubility of the phosgene is large at the time of phosgenation reaction, and solubility of hydrochloric acid is small. Examples of the high-boiling point organic aromatic compound can include 1,2-diethylbenzene, 1,3-diethylbenzene, 1,4-diethylbenzene, isopropylbenzene, 1,2,4-trimethylbenzene, amylbenzene, diamylbenzene, triamylbenzene, dodecylbenzene, p-cymene, cumene methyl phenyl ether, ethyl phenyl ether, diisoamyl ether, n-hexyl ether, orthodichlorobenzene, para-chlorotoluene, bromobenzene, 1,2,4-trichlorobenzene, and the like. In addition, the ester compound is not particularly limited, but ester acetate such as isoamyl acetate and isooctyl acetate is preferable. Among the solvent exemplified therein, a particularly preferable solvent to perform the present invention is an aromatic halogen compound.

In addition, after finishing the reaction, it is possible to perform general catalyst filtration, desolventizing, purification step, and the like, and to obtain a targeted isocyanate compound.

The isocyanate compound obtained by the present embodiment can be used as a raw material of an optical material and a coating material. The amine compound obtained by the present embodiment can be used as a coating material and a raw material of a curing agent.

EXAMPLES

Hereinafter, the present invention will be specifically described based on examples, and the present invention is not limited to the examples.

Evaluation of Increase in Temperature

In order to maintain a reaction temperature of 190° C. of a reaction solution in a reaction vessel 18, the temperature was increased in a jacket of the reaction vessel 18. Based on the following criteria, the temperature increased in the jacket (heat medium temperature) was evaluated.

A: Reaction temperature of less than −5° C.
B: Reaction temperature of equal to or more than −5° C. and less than +5° C.
C: Reaction temperature of equal to or more than +5° C. and less than +15° C.
D: Reaction temperature of equal to or more than +15° C.

Comparative Example 1

Consecutive production of cyanonorbornene was performed following the same flow as that of FIG. 1. A stirring tank type pressure resistant reactor (manufactured by SUS-304) having an inner volume of 150 liters with a stirrer and a jacket was used as a reaction vessel 18.

Before starting reaction, 100 liters of cyanonorbornene was charged in the reaction vessel 18, a heat medium oil heated by an electric heater was passed through the jacket of the reaction vessel 18 while stirring the stirrer at the number of revolution of 120 rpm, and a solution temperature in the reaction vessel 18 was increased to 190° C.

Subsequently, acrylonitrile was provided in a mixture vessel 16 by the amount shown in Table 1 from a tank 12 through a line 22, dicyclopentadiene was provided in the mixture vessel 16 by the amount shown in Table 1 from a tank 14 through a line 24, and dicyclopentadiene and acrylonitrile were mixed with each other at 1:2.5 in the mixture vessel 16. In the mixture solution, an amount of methyl bicyclononadiene was 0.02% by weight with respect to a total amount of 100% by weight of dicyclopentadiene, acrylonitrile, and methyl bicyclononadiene. The mixture solution in the reaction vessel 16 was consecutively provided in a liquid phase portion in the reaction vessel 18 from a raw material provision pipe (line 26) by a quantitative pump. A provision flow amount was adjusted such that the retention time was 1.2 hours. Reaction was performed while maintaining a liquid level in the reaction vessel 18 such that a volume of a gas phase portion of an upper layer of the reaction solution was 30% with respect to a total volume in the reaction vessel 18 during the reaction. In addition, at the same time, a pressure was adjusted such that the pressure in the reaction vessel 18 was 8 kg/cm²·G, the solution temperature was adjusted to maintain 190° C., and consecutive reaction was performed. As a result, an average yield of the obtained cyanonorbornene was 90% based on cyclopentadiene obtained by decomposition of dicyclopentadiene of a raw material, after 12 hours of starting of operation. In addition, regarding the reaction product, an amount of methyl bicyclononadiene was 0.02% by weight with respect to a total amount of 100% by weight of cyanonorbornene, methyl bicyclononadiene, and a non-reactive raw material (dicyclopentadiene and acrylonitrile).

The reaction product is consecutively provided to a flash device 20 through a line 28 from a reaction vessel 18, from a tower top portion, a mixture solution containing acrylonitrile and dicyclopentadiene which are non-reactive raw materials is recovered, and the reaction product is consecutively provided to a raw material recovering tower 21 from the flash device 20 through a line 30, and from the tower top portion, a mixture solution containing acrylonitrile and dicyclopentadiene which are non-reactive raw materials is recovered. The mixture solutions recovered from the flash device 20 and the raw material recovering tower 21 were returned to the mixture vessel 16 through a line 32 and circulation-recycled. The mixture solutions in the mixture vessel 16 was analyzed by gas chromatography, and was managed such that the amount of methyl bicyclononadiene was 0.02% by weight, as described above. On the other hand, from a tower bottom portion, cyanonorbornene with a purity of 97.3% by weight not containing non-reactive raw materials was separated.

The flash device was a pressure resistant device having an inner volume of 100 liters, and in the operating conditions, the temperature was 160° C., normal temperature.

The raw material recovering tower 21 was filled with a cascade mini-ring of 1 inch at a tower diameter of 12 inches and a height of 13.5 m, and the operating conditions were a tower bottom portion temperature of 143° C., a tower top portion pressure of 17.4 kPa, and a tower top portion temperature of 58° C.

As a result, a yield of cyanonorbornene based on fineness of dicyclopentadiene provided to the reaction vessel 18 was 99.6%, and a yield of cyanonorbornene based on acrylonitrile provided to the reaction vessel 18 was 99.4%.

Comparative Example 2

Using each component by the amount shown in Table 1, consecutive reaction was performed in the same manner as that of Comparative Example 1, except that, in the mixture solution, an amount of methyl bicyclononadiene was 0.01% by weight with respect to a total amount of 100% by weight of dicyclopentadiene, acrylonitrile, and methyl bicyclononadiene. As a result, an average yield of the obtained cyanonorbornene was 88% based on cyclopentadiene obtained by decomposition of dicyclopentadiene of a raw material, after 12 hours of starting operation. The result is shown in Table 1.

TABLE 1

| Composition | Comparative Example 1 | Comparative Example 2 |
|---|---|---|
| Content in mixture solution % by weight | | |
| Acrylonitrile | 45.6 | 45.7 |
| Dicyclopentadiene | 54.1 | 54.1 |
| Cyanonorbornene | 0 | 0 |
| Methyl bicyclononadiene | 0.02 | 0.01 |
| High-boiling point product | 0.01 | 0.01 |
| Elapse time after starting operation [h] | 12 | 12 |
| Reaction temperature [° C.] | 190 | 190 |
| Heat medium temperature [° C.] | 177 | 177 |
| Increase in temperature (evaluation) | A | A |
| Yield [%] | 90 | 88 |

Examples 1 to 3, Comparative Example 3

Using each component by the amount shown in Table 2, consecutive reaction was performed in the same manner as that of Comparative Example 1, except that, in the mixture solution, an amount of methyl bicyclononadiene was the amount shown in Table 2 with respect to a total amount of 100% by weight of dicyclopentadiene, acrylonitrile, and methyl bicyclononadiene. As a result, an average yield of the obtained cyanonorbornene was the amount shown in Table 2 based on cyclopentadiene obtained by decomposition of dicyclopentadiene of a raw material, after a predetermined elapse time of starting operation. The result is shown in Table 2.

TABLE 2

| Composition | Example 1 | Example 2 | Example 3 | Comparative Example 3 |
|---|---|---|---|---|
| Content in mixture solution % by weight | | | | |
| Acrylonitrile | 45.5 | 35.9 | 33.5 | 32.9 |
| Dicyclopentadiene | 42.7 | 33.6 | 31.4 | 30.9 |
| Cyanonorbornene | 3.2 | 6.8 | 7.1 | 7.2 |
| Methyl bicyclononadiene | 5.6 | 20.7 | 25 | 26 |
| High-boiling point product | 3 | 3 | 3 | 3.1 |
| Elapse time after starting operation [h] | 800 | 2450 | 2850 | 2850 |
| Reaction temperature [° C.] | 190 | 190 | 190 | 185 |
| Heat medium temperature [° C.] | 183 | 195 | 200 | 200 |
| Increase in temperature (evaluation) | A | C | C | D |
| Yield [%] | 97 | 95 | 93 | 91 |

Priority is claimed on Japanese Patent Application No. 2017-148428, filed on Jul. 31, 2017, the content of which is incorporated herein by reference.

The invention claimed is:

1. A process for producing cyanonorbornene, comprising:
   Step 1 of preparing a mixture solution including 0.5% by weight to 28% by weight of methyl bicyclononadiene, with respect to a total amount of 100% by weight of dicyclopentadiene, acrylonitrile, and the methyl bicyclononadiene, in a container; and
   Step 2 of reacting the dicyclopentadiene with the acrylonitrile in the presence of the methyl bicyclononadiene, in the mixture solution.

2. The process for producing cyanonorbornene according to claim 1, further comprising:
   after Step 2,
   Step 3 of obtaining cyanonorbornene and recovering the methyl bicyclononadiene and a non-reactive raw material, from a reaction product obtained in Step 2; and
   Step 4 of providing the recovered methyl bicyclononadiene and the non-reactive raw material to the container in Step 1 to reuse those,
   wherein Steps 1 to 4 are consecutively repeatedly performed.

3. The process for producing cyanonorbornene according to claim 1,
   wherein the reaction product obtained in Step 2 includes 0.5% by weight to 28% by weight of the methyl bicyclononadiene with respect to a total amount of 100% by weight of the cyanonorbornene, the methyl bicyclononadiene, and a non-reactive raw material.

4. The process for producing cyanonorbornene according to claim 1,
   wherein a reaction temperature in Step 2 is 160° C. to 220° C.

5. A process for producing an amine compound, comprising:
   a step of preparing cyanonorbornene by the process for producing according to claim 1;
   a step of causing hydroformylation reaction of the cyanonorbornene with carbon monoxide and hydrogen; and
   a step of causing imination by reacting an aldehyde compound obtained in the hydroformylation step with ammonia and reacting thereof with hydrogen in the presence of a catalyst.

6. A process for producing an isocyanate compound, comprising:
   a step of preparing an amine compound by the process for producing according to claim 5; and
   a step of reacting the amine compound with a carbonylating agent.

* * * * *